US007169401B2

(12) United States Patent
Puglia et al.

(10) Patent No.: US 7,169,401 B2
(45) Date of Patent: Jan. 30, 2007

(54) TOPICAL SKIN CARE COMPOSITION CONTAINING REFINED PEANUT OIL

(75) Inventors: Nancy Puglia, Sanford, FL (US); Jerry Roth, Sanford, FL (US); Rosario Ramirez, Sanford, FL (US)

(73) Assignee: Hill Dermaceuticals, Inc., Sanford, FL (US)

( * ) Notice: Subject to any disclaimer, the term of this patent is extended or adjusted under 35 U.S.C. 154(b) by 0 days.

(21) Appl. No.: 10/892,153

(22) Filed: Jul. 16, 2004

(65) Prior Publication Data

US 2005/0053635 A1     Mar. 10, 2005

Related U.S. Application Data

(63) Continuation-in-part of application No. 10/622,560, filed on Jul. 18, 2003, now abandoned.

(60) Provisional application No. 60/507,117, filed on Oct. 1, 2003.

(51) Int. Cl.
*A61K 6/00*     (2006.01)
*A61K 8/02*     (2006.01)

(52) U.S. Cl. .................................................. 424/401

(58) Field of Classification Search ................ 424/401
See application file for complete search history.

(56) References Cited

U.S. PATENT DOCUMENTS

| | | | |
|---|---|---|---|
| 3,966,924 A | 6/1976 | Fredriksson | |
| 4,296,130 A * | 10/1981 | Herschler | .................... 514/711 |
| 4,654,373 A | 3/1987 | Bertelli | |
| 4,737,360 A | 4/1988 | Allen et al. | |
| 4,857,321 A | 8/1989 | Thomas | |
| 4,992,478 A | 2/1991 | Geria | |
| 5,538,737 A | 7/1996 | Leonard et al. | |
| 5,573,781 A | 11/1996 | Brown et al. | |
| 5,626,873 A | 5/1997 | Weiner et al. | |
| 5,645,854 A | 7/1997 | Masiz | |
| 5,651,991 A | 7/1997 | Sugiyama et al. | |
| 5,656,672 A | 8/1997 | Collin et al. | |
| 5,660,837 A | 8/1997 | Lundquist | |
| 5,851,543 A | 12/1998 | Korb et al. | |
| 5,962,512 A | 10/1999 | Goupil | |
| 5,976,555 A | 11/1999 | Liu et al. | |
| 6,030,623 A | 2/2000 | Meade | |
| 6,080,393 A | 6/2000 | Liu et al. | |
| 6,267,985 B1 | 7/2001 | Chen et al. | |
| 6,365,656 B1 | 4/2002 | Green et al. | |
| 6,383,499 B1 | 5/2002 | Lipi | |
| 6,413,536 B1 | 7/2002 | Gibson et al. | |
| 6,423,323 B2 * | 7/2002 | Neubourg | .................... 424/401 |

OTHER PUBLICATIONS

Peanut Allergy, New England Journal of Medicine, 349;3:301-303.*
PCT International Search Report dated Aug. 27, 2004.
Lack et al., New Eng J Med, 348(11):977-85 (2003).
Lever, B Med J, 313:299-300 (1996).
Taylor et al., J Allergy Clin Immunol, 68(5):372-75 (1981).
PCT International Search Report dated Dec. 8, 2004.
Paller et al., Journal of American Academy of Dermatology, 48:40, 569-577 (Apr. 2003).
FDA: "Derma-Smoothe FS" Drug Approvals, 'Online!, pp. 1-8, Aug. 1999. Retrieved from the Internet: URL:http:/ww.fda.gov/cder/approval/index.htm.
Crevel et al., Food and Chemical Toxicology, 38:4, 385-393 (Apr. 2000).
Olszewski et al., Clinical and Experimental Allergy, 28:7, pp. 850-859 (Jul. 1998).
Koppelman et al., Journal of Biological Chemistry, 274:8, pp. 4770-4777 (Feb. 1999).

* cited by examiner

*Primary Examiner*—San-Ming Hui
(74) *Attorney, Agent, or Firm*—Bell, Boyd & Lloyd

(57) ABSTRACT

A vehicle containing refined peanut oil for topical use in skin care and for use in skin care therapeutics, and a process for making the vehicle and a composition and therapeutic composition made from that process.

14 Claims, No Drawings

TOPICAL SKIN CARE COMPOSITION CONTAINING REFINED PEANUT OIL

This application is a continuation-in-part of U.S. Ser. No. 10/622,560 filed 18 Jul. 2003 now abandoned. This application also claims benefit to U.S. Ser. No. 60/507,117 filed 1 Oct. 2003.

FIELD OF THE INVENTION

The invention relates generally to medicated skin treatment compositions and more particularly to a vehicle, such as a cream, lotion, balm, ointment, gel and the like containing a medicament for the treatment of a skin condition.

BACKGROUND OF THE INVENTION

Medicinal topical preparations can serve as drug delivery means. The vehicles thereof carry the pharmacologically active agents to the skin, but also can serve as a depot for delivery of the drugs intradermally or transdermally.

Other topical preparations do not serve to deliver a therapeutic agent but may serve to treat various skin conditions, by, for example, softening of the skin, tightening of the skin or moisturizing the skin.

There remains a need in the art for a therapeutic product and approach that can contain one or more active agents or medicines using a vehicle with beneficial properties. Such a vehicle, for example, a cream, would be one that has hydrating effects on human skin. Such a therapeutic carrier would ameliorate any drying, irritating or debilitating effect of the medicaments on the skin and thus, make the course of treatment more tolerable for the patient, improving patient compliance and thus, the therapeutic effectiveness of the pharmaceutically active agent(s).

SUMMARY OF THE INVENTION

The invention provides a skin care composition containing hypoallergenic or non-allergenic or refined peanut oil for topical application to the skin and particularly keratinized skin. The invention also provides a preparation containing non-allergenic or refined peanut oil for the topical application of a medicament to the skin and particularly keratinized skin. The medicament can be a skin care therapeutic. The invention also provides a process for making the vehicle.

DETAILED DESCRIPTION OF THE INVENTION

The instant invention relates to a novel and useful vehicle for topical non-pharmaceutical and pharmaceutical applications. The topical vehicle is a mixture, suspension or emulsion of a variety of hydrophobic and hydrophilic reagents. The instant formulation can be in the form of a cream, paste, unguent, lotion, ointment, gel, serum, balm, salve, mousse, and other known compositions.

The instant topical vehicle is one that carries superior and unexpected properties, such as excellent skin hydrating properties, and such properties are obtained by the inclusion of a non-allergenic, refined peanut oil in the vehicle. To obtain the enhanced skin hydrating properties of a formulation of interest, the topical vehicle preferably is for use on keratinized or cornified skin, as compared to non-keratinized or mucous membranes as found in the mouth, esophagus, anus and vagina.

It has been suspected that creams containing peanut oil may be a cause of nut allergy (Lever, British Medical Journal 313:299–300, 1996). A recent study revealed that infants sensitized to peanuts might have been exposed to peanut oil (Lack et al., New England Journal of Medicine 348:977–985, 2003). Yet, peanut oil can be found in certain compositions, such as in injectables, where the oil serves as a reservoir of a drug. Thus, there remains no appreciation of employing peanut oil that is non-allergenic, and there is no appreciation of the skin hydrating properties of non-allergenic, refined peanut oil in a topical formulation.

The refined peanut oil of interest is commercially available (Welch, Holme & Clark, Newark, N.J.). A refined peanut oil of interest is one that is suitable for pharmaceutical use and is substantially free of proteins, and particularly those proteins known to be allergenic in humans, such as the ara h glycoproteins. Thus, a peanut oil of interest is treated to deactivate, to remove the biological activity, and at the least, the immunogenicity of such proteins and thus essentially is hypoallergenic and preferably non-allergenic.

For example, a refined peanut oil of interest is treated with alkali (or other refining solution) and/or heat. Many peanut oil impurities, including the proteinaceous allergens can be hydrated, and then separated. A water washing can be used to remove such impurities, the bulk of which often are removed in the form of soaps, with the proteins attached or associated with the soaps. Alternatively, proteins and the like which are water soluble, are removed by partitioning into the aqueous phase.

The refined peanut oil of interest optionally then can be bleached to remove other impurities, such as colored compounds and other remaining impurities. Generally, the bleaching process involves adsorption onto a carrier, such as activated carbon or a silicate, such as clay, such as bentonite. Generally the refined oil is passed over a bed of adsorbent or the adsorbent is mixed in the oil and then removed.

The refined peanut oil of interest optionally then can be further treated with a steam distillation process, often under vacuum.

A refined peanut oil of interest can be exposed to all three of the above treatments, in the order of refining, bleaching and then vacuum steam distillation.

A refined peanut oil of interest can be treated by other methods, the goal being to inactivate or remove the peanut oil allergens.

Inactivation of the peanut oil allergens can be monitored using any of a variety of methods, for example, the tests available from Neogen (Lansing, Mich.). Antibody to the various ara h glycoproteins is commercially available or can be made practicing known immunology methods. Both polyclonal or monoclonal antibodies can be made and used. Current commonly used antibodies are polyclonal, being raised to a collection of peanut protein, and thus to a variety of allergens. The use of such antibodies for the detection of peanut allergens can rely on any of the known assay formats, such as an ELISA. Commercially available tests can detect as little as 2.5 parts per million (ppm) of peanut protein. Using an antibody directed to peanut proteins in an ELISA, the refined peanut oil of interest was found to contain less than 1 ppm of peanut protein.

Most topical preparations are substantially lipophilic but also may be an emulsion of both lipophilic and hydrophilic ingredients. An artisan would well recognize how to formulate such topical preparations containing refined peanut oil comprising hydrophilic reagents and hydrophobic (or lipophilic) reagents.

The topical preparation of interest contains at least 1% by weight of refined peanut oil, at least 2% by weight, at least 3% by weight, at least 4% by weight, at least 5% by weight, at least 6% by weight, at least 7% by weight, at least 8% by weight, at least 9% by weight or at least 10% by weight of refined peanut oil.

The topical formulation can contain at least 15% by weight of refined peanut oil, at least 20%, at least 25%, at least 30%, at least 35%, at least 40%, at least 45% or at least 50% or more by weight of refined peanut oil. The properties of the final vehicle and the compatibility thereof with the one or more pharmaceutically active agents incorporated therein will determine the amount of refined peanut oil used.

The compositions of the instant invention can comprise a wide range of components as known in the art. The "CTFA Cosmetic Ingredient Handbook", Second Edition, 1992, which is incorporated by reference herein in its entirety, describes a wide variety of cosmetic and pharmaceutical ingredients commonly used in the skin care industry, which are suitable for use in the compositions of the instant invention. Reference also can be made to U.S. Pat. Nos. 6,013,271; 6,267,985; 4,992,478; 5,645,854; 5,811,111; and 5,851,543. Examples of functional classes of ingredients are absorbents, abrasives, anti-acne agents, anticaking agents, antifoaming agents, antimicrobial agents, antioxidants, binders, biological additives, buffering agents, such as sodium hydroxide, sodium citrate and EDTA, bulking agents, chelating agents, chemical additives, colorants, cosmetic astringents, cosmetic biocides, denaturants, dispersants, deodorants, lubricants, drug astringents, external analgesics, fragrance components, such as menthol, moisturizers, flavorants, humectants, thickeners, such as carboxymethylcellulose, opacifying agents, platicizers, preservatives, such as dichlorobenzil alcohol, benzoic acid, methylparaben and phenyl, propellants, reducing agents, skin bleaching agents, opacifiers, such as zinc oxide, magnesium aluminum silicate and titanium dioxide, skin-conditioning agents (emollients, humectants, miscellaneous and occlusive), skin protectants, solvents, foam boosters, hydrotropes, solubilizing agents, suspending agents (nonsurfactant), gelling agents, such as petrolatum and mineral wax, sunscreen agents, ultraviolet light absorbers, and viscosity increasing agents (aqueous and nonaqueous).

In addition, the topical carrier may include a penetration enhancer defined as a material that increases the permeability of the skin to one or more active agents so as to enhance permeability of one or more active agents, such as dimethylsulfoxide, dimethyl formamide, dimethylacetamide, decylmethylsulfoxide and polyethylene glycols.

Lipids may be used in a topical preparation of interest. As is known in the art, oils may be derived from animals, plants, nuts, petroleum etc. Those derived from animals, plant seeds and nuts are similar to fats and consequently, and can contain one or a significant number of one or more polar acids and/or ester groups. Alternatively, oils derived from petroleum are usually aliphatic or aromatic hydrocarbons that are essentially free of polar substitution and therefore may be preferred for certain applications. It is preferable for the oil to be refined so as to be compatible with human tissue.

Other oil-based products that can be used include hydrocarbons or mineral fats obtained by the distillation of petroleum (petroleum jelly); vegetable oils and liquid triglycerides; animal fats or solid natural triglycerides; and waxes or solid ethers of fatty acids and organic alcohols. Lanolin or wool fats that are obtained from sheep wool and made up of fatty acids and cholesterol esters; and cetyl and stearyl alcohols, which are solid alcohols obtained by hydrogenation of their respective acids are also useable. Amphophilic compounds such as soaps or salts of fatty acids, that may be acidic or basic depending on whether the lipophilic group is anionic or cationic, sulfated alcohols which are semi-synthetic substances and synthetic surface active agents are known in the art and can be used in the topical preparation of interest. Glycerine is obtained from fats and, due to its hydrophobicity, has the property of extracting water from the surface of the mucosa or denuded skin. Glycerin does not damage intact skin. Because glycerine has hydrophilic properties, it is a useful humectant in a preparation of interest.

Other materials that may be used in a topical preparation of interest include liquid alcohols, liquid glycols, liquid polyalkylene glycols, liquid esters, liquid amides, liquid protein hydrosylates, liquid alkylated protein hydrosylates, liquid lanolin and lanolin derivatives, and other like materials. Particular examples include monohydric and polyhydric alcohols, e.g., ethanol, isopropanol, glycerol, sorbitol, 2-methoxyethanol, diethylene glycol, ethylene glycol, hexylene glycol, mannitol, cetyl alcohol and propylene glycol; ethers, such as diethyl or dipropyl ether; polyethylene glycols and methoxypolyoxyethylenes; carbowaxes having molecular weights ranging from 200 to 20,000; polyoxyethylene glycerols; polyoxyethylene; sorbitols; and stearoyl diacetin. The topical carriers often include both an alcohol and water so as to accommodate lipophilic and hydrophilic components.

A number of different emulsifiers or surfactants can be used to prepare a topical preparation of interest. Emulsifiers can be ionic or non-ionic. Examples of amphoteric surfactants useful in the compositions of the instant invention include those disclosed in McCutcheon's, "Detergents and Emulsifiers", North American edition (1986) and McCutcheon's, "Functional Materials", North American Edition (1992); both of which are incorporated by reference herein in their entirety. Surfactants that can used include the betaines, sultaines and hydroxysultaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl bis-(2-hydroxyethyl) carboxymethyl betaine, steryl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, stearyl betaine, lauryl dimethyl sulfoethyl betaine, lauryl bis-(2-hydroxyethyl) sulfopropyl betaine, and amidobetaines and amidosulfobetaines, oleyl betaine, and cocamidopropyl betaine). Examples of sultaines and hydroxysultaines include cocamidopropyl hydroxysultaine. Examples of other amphoteric surfactants are alkyliminoacetates, iminodialkanoates and aminoalkanoates.

Examples of anionic surfactants also are disclosed in McCutcheon's, "Detergents and Emulsifiers", North American edition (1986) and McCutcheon's, "Functional Materials", North American Edition (1992). Examples include the alkoyl isethionates, and the alkyl and alkyl ether sulfates, such as, ammonium cocoyl isethionate, sodium cocoyl isethionate, sodium lauroyl isethionate, sodium stearoyl isethionate and mixtures thereof, the sarcosinates, such as sodium lauroyl sarcosinate, sodium cocoyl sarcosinate, and ammonium lauroyl sarcosinate, sodium lauryl sulfate, ammonium lauryl sulfate, ammonium cetyl sulfate, sodium cetyl sulfate, sodium stearyl sulfate, ammonium cocoyl isethionate, sodium lauroyl isethionate, sodium lauroyl sarcosinate, and mixtures thereof.

The instant vehicle can be used alone or as a carrier for one or more pharmaceutically active agents for topical use, preferably on keratinized skin. Examples of active agents include, vitamins, such as A, D, E and K, corticosteroids, hormones, anti-metabolites, cytostatic agents, alkylating agents, antimicrobials, such as antibacterials, antifungals and antivirals, keratolytics and the like. The amounts of the active agent are as known in the art or which can be determined empirically as known in the art.

A wide variety of cytostatic agents may be used. Examples include alkylating agents, enzyme inhibitors, proliferation inhibitors, DNA synthesis inhibitors, lytic agents, DNA intercalators, antimetabolites and the like. Illustrative agents include steroids, paclitaxel, ionomycin, etoposide, nitrosoureas such as carmustine, doxorubicin, daunorubicin, actinomycin D, meclorethamine, busulfan, chlorambucil, cactinomycin, carzinophilin, chlomaphazine, 6-chloropurine, azathioprine, fluorouracil, hydroxyurea, thioquanine, campothecin, mitomycin, lomustine, semustine, cantharidin, camptothecin, carboplatin, ricin, pseudomonas exotoxin, interferons, interleukins, TNF, vincristine, methehlorethamine, plicamycin, nitracine, nitoxantrone, methotrexate, nogalamycin, streptonigrin, streptozocin, tegafur, tetramin, testolactone, demecolcine and dactinomycin. Other compounds that can be used include cytophamide, cyclosporin, amsacrine, biantrene hydrochloride, camostat mesylate, campothecin, enocitabine, etoposide, epirubicin hydrochloride, fludarabine phosphate, flutamide, fotemustine, idarubicin hydrochloride, ionomycin, onidamine, mitoxantrone hydrochloride, nilutamide, paclitaxel, pirarubicin, toremifene, vinorelbine, didemnin, bactracyclin, mitoquidone, penclomedine, phenazinomycin, U-73975, saintopin, 9-aminocamptothecin, amonafide, merbarone and the like. Additional agents that can be used include mitomycin C, cisplatin, mechlorethamine, pyrazine diazohydroxide, fumagillin, rhyzoxin, dynemicin A, chlorambucil, semustine and the like.

Corticosteroids including halogenated corticosteroids that can be used in the topical preparations of interest generally are known and are commercially available. Examples include cortisone, hydrocortisone and derivatives thereof including cortodoxone, flucetonide, fludrocortisone acetate, flurandrenolone acetonide, medrysone; prednisone, prednisolone and derivatives thereof including amcinafal, amcinafide, betamethasone benzoate, valerate and dipropionate, chloroprednisone acetate, descinalone acetonide, desonide, dexamethasone, dichlorisone acetate, difluprednate, flucloronide, flumethasone, flunisolide acetate, fluocinolone acetonide, fluocinonide, fluocortolone, fluorometholone, fluperoline acetate, fluprednisolone valerate, meprednisone, methyl prednisolone, paramethasone acetate, prednisolomate, prednisolone acetate, butylacetate and phosphate sodium, triamcinolone acetonide, hexacetonide, diacetate, hydrocortisone butyrate, flumethasone pivalate, halcininide and clobetasol propionate.

Examples of other active ingredients that can be used in a topical preparation of interest include acebutolol, acetaminophen, acetohydoxamic acid, acetophenazine, acyclovir, allopurinol, alprazolam, aluminum hydroxide, amantadine, ambenonium, amiloride, aminobenzoate potassium, amobarbital, amoxicillin, amphetamine, ampicillin, androgens, anesthetics, anticoagulants, anticonvulsants, antithyroids, appetite suppressants, aspirin, atenolol, atropine, azatadine, bacampicillin, baclofen, beclomethasone, belladonna, bendroflumethiazide, benzoyl peroxide, benzthiazide, benztropine, bethanechol, biperiden, bisacodyl, bromocriptine, bromodiphenhydramine, brompheniramine, buclizine, bumetanide, busulfan, butabarbital, butaperazine, caffeine, calcium carbonate, captopril, arbamazepine, carbenicillin, carbidopa & levodopa, carbinoxamine inhibitors, carbonic anhydrase, carisoprodol, carphenazine, cascara, cefaclor, cefadroxil, cephalexin, cephradine, chlophedianol, chloral hydrate, chlorambucil, chloramphenicol, chlordiazepoxide, chloroquine, chlorothiazide, chlorotianisene, chlorpheniramine, chlorpromazine, chlorpropamide, chlorprothixene, chlorthalidone, chlorzoxazone, cholestyramine, cimetidine, cinoxacin, clemastine, clidinium, clindamycin, clofibrate, clomiphere, clonidine, clorazepate, cloxacillin, colchicine, coloestipol, estrogens, contraceptives, androgens, cromolyn, cyclacillin, cyclandelate, cyclizine, cyclobenzaprine, cyclophosphamide, cyclothiazide, cycrimine, cyproheptadine, danazol, danthron, dantrolene, dapsone, dextroamphetamine, dexchlorpheniramine, dextromethorphan, diazepan, dicloxacillin, dicyclomine, diethylstilbestrol, diflunisal, digitalis, diltiazen, dimenhydrinate, dimethindene, diphenhydramine, diphenidol, diphenoxylate, diphenylopyraline, dipyradamole, disopyramide, disulfiram, divalporex, docusate calcium, docusate potassium, docusate sodium. doxyloamine, dronabinol ephedrine, epinephrine, ergoloidmesylates, ergonovine, ergotamine, erythromycins, estropipute, etharynic acid, ethchlorvynol, ethopropazine, ethosaximide, ethotoin, fenoprofen, ferrous fumarate, ferrous gluconate, ferrous sulfate, flavoxate, flecainide, fluphenazine, fluprednisolone, flurazepam, folic acid, furosemide, gemfibrozil, glipizide, glyburide, glycopyrrolate, gold compounds, griseofuwin, guaifenesin, guanabenz, guanadrel, guanethidine, halazepam, haloperidol, hetacillin, hexobarbital, hydralazine, hydrochlorothiazide, hydroflunethiazide, hydroxychloroquine, hydroxyzine, hyoscyamine, ibuprofen, indapamide, indomethacin, insulin, iofoquinol, iron-polysaccharide, isoetharine, isoniazid, isopropamide, isoproterenol, isotretinoin, isoxsuprine, kaolin, pectin, ketoconazole, lactulose, levodopa, lincomycin, liothyronine, liotrix, lithium, loperamide, lorazepam, magnesium hydroxide, magnesium sulfate, magnesium trisilicate, maprotiline, meclizine, medofenamate, medroxyproyesterone, melenamic acid, melphalan, mephenytoin, mephobarbital, meprobamate, mercaptopurine, mesoridazine, metaproterenol, metaxalone, methamphetamine, methaqualone, metharbital, methenamine, methicillin, methocarbamol, methotrexate, methsuximide, methyclothinzide, methylcellulose, methyldopa, methylergonovine, methylphenidate, methylprednisolone, methysergide, metoclopramide, metolazone, metoprolol, metronidazole, minoxidil, mitotane, monamine oxidase inhibitors, nadolol, nafcillin, nalidixic acid, naproxen, narcotic analgesics, neomycin, neostigmine, niacin, nicotine, nifedipine, nitrates, nitrofurantoin, nomifensine, nylidrin, nystatin, orphenadrine, oxacillin, oxazepam, oxprenolol, oxymetazoline, oxyphenbutazone, pancrelipase, pantothenic acid, papaverine, paraaminosalicylic acid, paregoric, pemoline, penicillamine, penicillins, pentobarbital, perphenazine, phenacetin, phenazopyridine, pheniramine, phenobarbital, phenolphthalein, phenprocoumon, phensuximide, phenylbutazone, phenylephrine, phenylpropanolamine, phenyl toloxamine, phenytoin, pilocarpine, pindolol, piperacetatine, piroxicam, poloxamer, polycarbophil calcium, polythiazide, potassium supplements, pruzepam, prazosin, primidone, probenecid, probucol, procainamide, procarbazine, prochlorperazine, procyclidine, prornazine, promethazine, propantheline, propranolol, pseudoephedrine, psoralens, psyllium, pyridostigmine, pyrodoxine, pyrilamine, pyrvinium, quinestrol, quinethazone, quinidine, quinine, ranitidine, rauwolfia alkaloids, riboflavin, rifampin, ritodrine, salicylates, scopolamine, secobarbital, senna, sannosides, simethicone, sodium bicarbonate, sodium phosphate, sodium fluoride, spironolactone, sucrulfate, sulfacytine, sulfamethoxazole, sulfasalazine, sulfinpyrazone, sulfisoxazole, sulindac, talbutal, tamazepam, terbutaline, terfenadine, terphinhydrate, teracyclines, thiabendazole, thiamine, thioridazine, thiothixene, thyroblobulin, thyroid, thyroxine, ticarcillin, timolol, tocainide, tolazamide, tolbutamide, tolmetin, trozodone, tretinoin, triamcinolone, trianterene, triazolam, trichlormethiazide, tricyclic antidepressants, trifluoperazine, triflupromazine, trihexyphenidyl, trimeprazine, trimethobenzamine, trimethoprim, tripclennamine, triprolidine, valproic acid, verapamil and xanthine.

Suitable keratolytic agents include salicylic acid, derivatives of salicylic acid such as 5-octanoyl salicylic acid, and resorcinol; retinoids such as retinoic acid and derivatives thereof (e.g., cis and trans); sulfur-containing D and L amino acids and derivatives and salts thereof, particularly N-acetyl derivatives, such as N-acetyl-L-cysteine; lipoic acid; antibiotics and antimicrobials such as benzoyl peroxide, actopirox, tetracycline, trichlorobanilide, azelaic acid, phenoxyethanol, phenoxypropanol, phenoxyisopropanol, ethyl acetate, clindamycin and meclocycliue; sebostats such as flavonoids; and bile salts such as scymnol sulfate and derivatives thereof, deoxycholate and cholate.

Examples of antiwrinkle and antiskin atrophy actives that can be used in the topical preparations of interest include retinoic acid and derivatives; retinol; retinyl esters; salicylic acid and derivatives thereof; sulfur-containing D and L, amino acids and their derivatives and salts, particularly the N-acetyl derivatives, thiols, e.g. ethane thiol; alpha-hydroxy acids, e.g. glycolic acid, and lactic acid; phytic acid, lipoic acid; lysophosphatidic acid, and skin peel agents, e.g., phenol.

Examples of non-steroidal anti-inflammatories that can be used in the instant invention include propionic acid derivatives; acetic acid derivatives; fenamic acid derivatives; biphenylcarboxylic acid derivatives; and oxicams, and include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen and bucloxis acid.

Examples of topical anesthetic drugs that can be used in the topical preparation of interest include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Some medicaments, pharmaceuticals and drugs that can be used for dermatological uses, or which previously may not have been amenable to dermatologic use for any of a variety of reasons, can be irritating to the skin or can have other debilitating effects. For example, fluorouracil is irritating to skin.

The refined peanut oil-containing formulations of interest can overcome or mitigate those side effects because of the unexpected and beneficial skin hydrating property of refined peanut oil. The formulations of interest enhance intradermal and transdermal penetration of the pharmacologically active agent or agents, minimize residence time of same on the skin and minimize untoward side effects. Those results are obtained in part, by the hydrating effect of refined peanut oil on skin.

In the various embodiments, the compositions of the invention are useful for application to any subject in need thereof. The subject can be any vertebrate, especially a mammal, and most especially a human. The composition is amenable to self-application. The amounts used are essentially as known in the art, although amounts can be modified based on empirical data and routine experimentation.

Other features, objects, and advantages of the invention will be apparent from the description and from the claims. In the specification and the appended claims, the singular forms include plural references unless the context clearly dictates otherwise. Unless defined otherwise, all technical and scientific terms used herein have the same meaning as commonly understood by one of ordinary skill in the art to which this invention belongs.

The following EXAMPLES are presented to more fully illustrate the invention. The EXAMPLES should in no way be construed as limiting the scope of the invention, as defined by the appended claims.

EXAMPLE 1

Test of Hydrating Effects on Human Skin by Refined Peanut Oil

A test was performed to determine whether pure peanut oil or a corticoid oil formulation and its components could improve hydrating effects on human skin. The measuring was performed using biometric techniques. Transepidermal water loss (TEWL) was used as a parameter of monitoring the irritant response and capacitance as parameters of skin hydration. The side effects were also observed in the test. The testing was done by visual grading and by bioengineering techniques on ten healthy subjects (3 male and 7 female, mean ages 45±9). The results showed that plain peanut oil, the corticoid oil formulation containing peanut oil and the moisturizing vehicle containing peanut oil significantly improve skin hydration after one application.

Three parameters were selected to evaluate the effects of test formulations:

Clinical visual scoring (scaling; adverse effect—if any):

| | |
|---|---|
| 0 | none |
| 1 | slight (weak spotty erythema) |
| 2 | moderate erythema |
| 3 | severe erythema with edema or palpable infiltration |

Transepidermal water loss (TEWL) was assessed by a Tewameter (Tewameter TM 210, Courage, Cologne, Germany, and Acaderm Inc., Menlo Park, Calif.). TEWL documents integrity of stratum corneum water barrier function and is a sensitive indicator of skin water barrier alteration. The value of TEWL was expressed $g/m^2$ per h.

Skin hydration (i.e., electrical capacitance) was measured by a Corneometer (CM 820, Courage & Khazaka, Cologne, Germany). Capacitance was expressed digitally in arbitrary units (a.u.).

The measurements were conducted in a room with daily ranges of relative humidity (RH) from 55.0±4.6% and temperature from 18.4±0.5° C. The values (RH and ° C.) were recorded daily. Each subject was rested at least 30 min for acclimation before measurements.

Basal values of TEWL and capacitance were measured on each test site prior to treatment with test materials. The flexor aspects of both forearms of subjects were used for testing. The test sites on the left and right forearm of each subject were randomized. One test site served as normal skin control (without treatment). Other sites were wetted by spraying distilled water (approximately 0.1 ml) over a 3 cm$^2$ skin surface area. This saturation procedure was repeated on the same site each 5 minutes, for a total of 3 applications. Five minutes after the last application, 0.2 ml of a corticoid oil formulation (Derma-Smooth/FS®, Hill Dermaceuticals, Sanford, Fla.), a moisturizing vehicle and plain peanut oil were applied to the each pre-designated site (3 cm$^2$). One site was kept blank as a control (water saturation only). Thirty minutes later, the test sites were gently wiped with paper tissues, and then clinical scores, TEWL, and capacitance were recorded at each test site. These were repeated at 2 and 3 hours.

Statistics were performed using a computer program SigmaStat® (SPSS Science, Chicago, Ill.). Values of TEWL and capacitance between blank plus water only site and other test sites were analyzed with the paired t test. One-way repeated-measures ANOVA was utilized to evaluate the differences among the plain peanut oil, the corticoid oil formulation and the moisturizing vehicle-treated sites. Levels of significance were marked as follows: *$p<0.05$, $p<0.01$, *$p<0.001$.

The results showed that plain peanut oil significantly improved skin hydration after 30 minutes of each single application as compared to water or no treatment. There was no statistical difference between plain peanut oil, the moisturizing vehicle that contains peanut oil and the corticoid oil formulation that contains peanut oil.

No VS alternation was observed.

Hydrated skins can increase the penetration of applied medicaments or active ingredients, such as fluocinolone acetonide.

EXAMPLE 2

A cream was prepared with the following ingredients in the amounts indicated.

TABLE 1

| Ingredient | 800 g Batch Quantity | Formula |
|---|---|---|
| magnesium aluminum silicate NF | 24 g | 3.00% |
| butylated hydroxytoluene NF | 320 mg | 0.04% |
| cetyl alcohol NF | 32 g | 4.00% |
| stearic acid NF | 24 g | 3.00% |
| stearyl alcohol NF | 32 g | 4.00% |
| methylparaben NF | 1.440 g | 0.18% |
| propylparaben NF | 160 mg | 0.02% |
| Arlacel ® 165 [glycerol stearate and PEG-100 stearate glycerol monostearate] | 28 g | 3.50% |
| methyl glucetʰ-10 | 32 g | 4.00% |
| glycerin USP | 24 g | 3.00% |
| isopropyl myristate | 32 g | 4.00% |
| peanut oil NF refined | 40 g | 5.00% |
| tretinoin USP | 400 mg | 0.05% |
| fluocinolone acetonide USP | 80 mg | 0.01% |
| citric acid USP | 400 mg | 0.05% |
| hydroquinone USP | 32 g | 4.00% |
| sodium metabisulfite NF | 1.6 g | 0.20% |
| purified water USP | 495.60 g | 61.95% |
| Total | | 100.00% |

Fluocinolone acetonide is a synthetic fluorinated corticosteroid for topical dermatological use and is classified therapeutically as an anti-inflammatory. It is a white crystalline powder that is odorless and stable in light. The chemical name for fluocinolone acetonide is (6,11,16)-6,9-difluoro-11,21-dihydroxy-16,17-[(1-methylethylidene)bis (oxy)]-pre gna-1,-4-diene-3,20-dione. The molecular formula is $C_{24}H_{30}F_2O_6$ and the molecular weight is 452.5. The amount of fluocinolone acetonide in the composition of the invention can be in an amount understood by those of skill in the art to be effective. In particular, the amount can be in the range of between 0.005% and 0.02%.

Tretinoin is all-trans-retinoic acid formed from the oxidation of the aldehyde group of retinene to a carboxyl group. It is highly reactive to light and moisture. Tretinoin is classified therapeutically as a keratolytic. The chemical name for tretinoin is (all-E)-3,7-dimethyl-9-(2,6,6-trimethyl-1-cyclohexen-1-yl)-2,4,6,8-nonatetraenoic acid. The molecular formula is $C_{20}H_{28}O_2$ and the molecular weight is 300.44. The amount of tretinoin in the composition of the invention can be in amount understood by those of skill in the art to be effective. In particular, the amount can be in the range of between 2% and 10%.

Hydroquinone is classified therapeutically as a depigmenting agent. It is prepared from the reduction of ρ-benzoquinone with sodium bisulfite. It occurs as fine white needles that darken on exposure to air. The chemical name for hydroquinone is 1,4-benzenediol. The molecular formula is $C_6H_6O_2$ and the molecular weight is 110.11. The amount of hydroquinone in the composition of the invention can be in amount understood by those of skill in the art to be effective. In particular, the amount can be in the range of between 0.02% and 0.1%.

The method for making a therapeutic cream employs the following steps:

To a 1000 ml beaker add:

| | |
|---|---|
| water | 495.6 g |
| magnesium aluminum silicate NF | 24 g |
| butylated hydroxytoluene | 0.32 g |

Heat this mixture to 75–80° C. with continued mixing.
To a 400 ml beaker add:

| | |
|---|---|
| cetyl alcohol | 32 g |
| stearic acid | 24 g |
| stearyl alcohol | 32 g |
| methyl glueth-10 | 32 g |
| methylparaben | 1.44 g |
| propylparaben | 0.16 g |
| glycerin | 24 g |
| isopropyl myristate | 32 g |
| peanut oil | 40 g |

Heat this mixture to 75–80° C. and mix until dissolved.
With good agitation transfer the mixture in the 400 ml beaker to the 1000 ml beaker. Allow cooling to begin.
When the temperature reaches 70° C. add:

| | |
|---|---|
| Arlacel ® 165 | 28 g |
| tretinoin | 0.4 g |
| fluocinolone acetonide | 0.08 g |

Continue mixing and cooling.
When the temperature reaches 60° C. add:

| | |
|---|---|
| citric acid anhydrous | 0.4 g |

When the temperature reaches 55° C. add:

| | |
|---|---|
| hydroquinone | 32 g |

Continue mixing and cooling.

When the temperature reaches 50° C., place the beaker under a counter top homogenizer. Start the homogenizer and continue mixing and cooling.

When the temperature reaches 45° C. add:

| | |
|---|---|
| sodium metabisulfite | 1.6 g |

Continue mixing and cooling.

Mix the completed batch for at least 30 minutes.

The resulting composition of the invention can be stored at controlled room temperature of 68 to 77° F. (20–25° C.).

EXAMPLE 3

In another embodiment, the composition contains tretinoin (0.05%) as the medicament in a cream base containing isopropyl myristate and refined peanut oil. This embodiment is useful for the treatment of acne.

TABLE 2

| Ingredient | 800 g Batch Quantity | Formula |
|---|---|---|
| magnesium aluminum silicate NF | 24.00 g | 3.00% |
| butylated hydroxytoluene NF | 1.60 mg | 0.20% |
| cetyl alcohol NF | 32.00 g | 4.00% |
| stearic acid NF | 24.00 g | 3.00% |
| stearyl alcohol NF | 32.00 g | 4.00% |
| methylparaben NF | 1.44 g | 0.18% |
| propylparaben NF | 0.16 g | 0.02% |
| Arlacel ® 165 [glycerol stearate and PEG-100 stearate glycerol monostearate] | 28.00 g | 3.50% |
| methyl gluceth-10 | 32.00 g | 4.00% |
| glycerin USP | 24.00 g | 3.00% |
| isopropyl myristate | 32.00 g | 4.00% |
| peanut oil NF refined | 40.00 g | 5.00% |
| tretinoin USP | 0.40 g | 0.05% |
| citric acid USP anhydrous | 0.40 g | 0.05% |
| purified water USP | 528.00 g | 66.00% |
| Total | | 100.00% |

EXAMPLE 4

In another embodiment, the composition contains hydroquinone (4.0%) as the medicament in a cream base containing isopropyl myristate and peanut oil. This embodiment is useful for the treatment of hyperpigmentation or postinflammatory conditions. An embodiment is provided in TABLE 3.

TABLE 3

| Ingredient | 800 g Batch Quantity | Formula |
|---|---|---|
| magnesium aluminum silicate NF | 24.00 g | 3.00% |
| butylated hydroxytoluene NF | 0.320 g | 0.04% |
| cetyl alcohol NF | 32.00 g | 4.00% |
| stearic acid NF | 24.00 g | 3.00% |
| stearyl alcohol NF | 32.00 g | 4.00% |
| methylparaben NF | 1.44 g | 0.18% |
| propylparaben NF | 0.16 g | 0.02% |
| Arlacel ® 165 [glycerol stearate and PEG-100 stearate glycerol monostearate and polyoxyethylene stearate] | 28.00 g | 3.50% |
| methyl gluceth-10 | 32.00 g | 4.00% |
| glycerin USP | 24.00 g | 3.00% |
| isopropyl myristate | 32.00 g | 4.00% |
| peanut oil NF refined | 40.00 g | 5.00% |
| citric acid USP anhydrous | 0.40 g | 0.05% |
| hydroquinone USP | 32.00 g | 4.00% |
| sodium metabisulfite NF | 1.60 g | 0.20% |
| purified water USP | 527.52 g | 65.94% |
| Total | | 100.00% |

EXAMPLE 5

In another embodiment, the composition contains fluocinolone acetonide (0.01%) as the medicament in a cream base containing isopropyl myristate and refined peanut oil. This embodiment is useful for the treatment of inflammatory conditions. An embodiment is provided in TABLE 4.

TABLE 4

| Ingredient | 800 g Batch Quantity | Formula |
|---|---|---|
| magnesium aluminum silicate NF | 24.00 g | 3.00% |
| butylated hydroxytoluene NF | 0.320 g | 0.04% |
| cetyl alcohol NF | 32.00 g | 4.00% |
| stearic acid NF | 24.00 g | 3.00% |
| stearyl alcohol NF | 32.00 g | 4.00% |
| methylparaben NF | 1.44 g | 0.18% |
| propylparaben NF | 0.16 g | 0.02% |
| Arlacel ® 165 [glycerol stearate and PEG-100 stearate glycerol monostearate and polyoxyethylene stearate] | 28.00 g | 3.50% |
| methyl gluceth-10 | 32.00 g | 4.00% |
| glycerin USP | 24.00 g | 3.00% |
| isopropyl myristate | 32.00 g | 4.00% |
| peanut oil NF refined | 40.00 g | 5.00% |
| citric acid USP anhydrous | 0.40 g | 0.05% |
| fluocinolone acetonide USP | 80.0 mg | 0.01% |
| sodium metabisulfite NF | 1.60 g | 0.20% |
| purified water USP | 528 g | 66% |
| Total | | 100.00% |

The foregoing description has been presented only for the purposes of illustration and is not intended to limit the invention to the precise form disclosed, but by the claims appended hereto.

All patents and publications cited in this specification are incorporated by reference herein in entirety.

What is claimed is:

1. A skin hydrating medicament comprising:
    (a) a cream base for topical use consisting essentially of a refined peanut oil; and
    (b) an active ingredient, wherein said active ingredient is fluorouracil.

2. The medicament of claim 1, wherein said refined peanut oil is present in a range of between about 1% and about 10% by weight.

3. The medicament of claim 1, wherein said refined peanut oil is produced by alkali treatment.

4. The medicament of claim 1, wherein said refined peanut oil is produced by heat treatment.

5. A medicament comprising a skin hydrating cream base consisting essentially of a hypoallergenic peanut oil, and an active ingredient, wherein said active ingredient is fluorouracil.

6. The medicament of claim 5, wherein said hypoallergenic peanut oil is present in a range of between about 1% and about 10% by weight.

7. The medicament of claim 5, wherein said hypoallergenic peanut oil is produced by alkali treatment.

8. The medicament of claim 5, wherein said hypoallergenic peanut oil is produced by heat treatment.

9. The medicament of claim 5, wherein said hypoallergenic peanut oil is non-allergenic.

10. A medicament comprising a skin hydrating cream base consisting essentially of a treated peanut oil, and an active ingredient, wherein said active ingredient is fluorouracil and wherein said treated peanut oil contains less than 1 part per million peanut protein.

11. The medicament of claim 10, wherein said peanut protein is an ara h protein.

12. The medicament of claim 10, wherein said treated peanut oil is present in a range of between about 1% and about 10% by weight.

13. The medicament of claim 10, wherein said treated peanut oil is produced by alkali treatment.

14. The medicament of claim 10, wherein said treated peanut oil is produced by heat treatment.

* * * * *